United States Patent
Price et al.

(10) Patent No.: US 7,104,977 B2
(45) Date of Patent: Sep. 12, 2006

(54) PERSONAL PRODUCT EMERGENCY KIT

(75) Inventors: Cindy Lou Price, Appleton, WI (US); Barbara Lynn Chancellor, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/974,143

(22) Filed: Oct. 27, 2004

(65) Prior Publication Data

US 2006/0089612 A1    Apr. 27, 2006

(51) Int. Cl.
A61F 13/15 (2006.01)

(52) U.S. Cl. .......... 604/385.06; 604/359; 604/385.26; 206/581

(58) Field of Classification Search .......... 604/385.06, 604/359, 385.01, 385.26, 385.28; D24/126; 206/581, 524.8
See application file for complete search history.

(56) References Cited

U.S. PATENT DOCUMENTS

| | | |
|---|---|---|
| 3,594,820 A | 7/1971 | Mccurry |
| 3,636,953 A | 1/1972 | Benevento |
| 3,887,103 A | 6/1975 | Spooner |
| 3,970,217 A | 7/1976 | Culbertson et al. |
| 4,221,221 A | 9/1980 | Ehrlich |
| D285,906 S | 9/1986 | Tyler |
| 4,685,559 A | 8/1987 | Titus |
| 4,698,855 A | 10/1987 | Hicks |
| 4,702,378 A | 10/1987 | Finkel et al. |
| 4,706,845 A | 11/1987 | Schnurer et al. |
| 4,720,021 A | 1/1988 | Byrns |
| 4,792,024 A | 12/1988 | Morton et al. |
| 4,883,481 A | 11/1989 | Blanchard |
| D310,748 S | 9/1990 | Embree et al. |
| 4,961,522 A | 10/1990 | Weber |
| 4,964,859 A | 10/1990 | Feldman |
| D314,279 S | 2/1991 | Hotchkiss |
| 5,036,997 A | 8/1991 | May et al. |
| 5,071,414 A | 12/1991 | Elliott |
| 5,117,979 A | 6/1992 | Brightbill |
| D329,135 S | 9/1992 | Embree |
| D330,161 S | 10/1992 | Schuh |
| 5,230,450 A | 7/1993 | Mahvi et al. |
| 5,255,817 A | 10/1993 | Reiland et al. |
| D341,027 S | 11/1993 | Godden et al. |
| 5,261,531 A | 11/1993 | Nieves |

(Continued)

FOREIGN PATENT DOCUMENTS

GB    2 392 098 A    2/2004

(Continued)

OTHER PUBLICATIONS

"Baby on the Go," Internet web page "www.babygo.net/news2.html", Earth Angels International, Inc., viewed and printed prior to Oct. 2004, 1 page.

(Continued)

*Primary Examiner*—Jacqueline F. Stephens
(74) *Attorney, Agent, or Firm*—Paul Yee

(57) ABSTRACT

A personal care system (80) comprises a plurality of kit items, and an assembly mechanism (82) which holds the kit items together in a cooperating, combined unit. In a particular aspect, the kit items can include a substitute undergarment (20), and a supplemental absorbent article (34) configured to cooperate with the substitute undergarment (20). In further aspects, the system can also include a first treatment-component (56) configured to provide a first treatment-type, along with at least a second treatment-component (58) configured to provide a second treatment-type that differs from the first treatment-type.

19 Claims, 10 Drawing Sheets

U.S. PATENT DOCUMENTS

| | | | |
|---|---|---|---|
| 5,370,263 A | 12/1994 | Brown | |
| D357,119 S | 4/1995 | Calmeise et al. | |
| 5,409,105 A | 4/1995 | Appelbaum et al. | |
| 5,421,459 A | 6/1995 | Mazzotti | |
| 5,433,373 A | 7/1995 | Zoeller | |
| 5,443,161 A | 8/1995 | Jonese | |
| D367,172 S | 2/1996 | Brightbill et al. | |
| D367,609 S | 3/1996 | Frank et al. | |
| D371,030 S | 6/1996 | Hall | |
| 5,569,230 A | 10/1996 | Fisher et al. | |
| 5,575,784 A | 11/1996 | Ames-Ooten et al. | |
| 5,579,916 A | 12/1996 | Manko | |
| 5,582,605 A | 12/1996 | Lepie | |
| 5,624,095 A | 4/1997 | Zissu | |
| 5,638,957 A | 6/1997 | Brasier | |
| 5,655,680 A | 8/1997 | Asbach et al. | |
| 5,678,727 A | 10/1997 | Rice | |
| 5,702,140 A | 12/1997 | Radja | |
| 5,706,950 A | 1/1998 | Houghton et al. | |
| 5,707,031 A | 1/1998 | Creighton-Young | |
| 5,875,490 A | 3/1999 | Woodard et al. | |
| 5,884,771 A | 3/1999 | Mccormick | |
| D412,439 S | 8/1999 | Cormack | |
| 6,004,307 A | 12/1999 | Colon et al. | |
| 6,105,170 A | 8/2000 | Lisciandro et al. | |
| 6,168,022 B1 | 1/2001 | Ward et al. | |
| 6,182,022 B1 | 1/2001 | Mayle et al. | |
| 6,213,304 B1 | 4/2001 | Juilussen | |
| 6,298,993 B1 | 10/2001 | Kalozdi | |
| 6,367,089 B1 | 4/2002 | Van Gompel et al. | |
| 6,616,649 B1 * | 9/2003 | Ismail | 604/393 |
| 6,723,080 B1 | 4/2004 | Habib et al. | |
| 6,745,895 B1 | 6/2004 | Silvers | |
| 2003/0136704 A1 | 7/2003 | Burgess | |
| 2004/0025219 A1 | 2/2004 | Mcqueen | |
| 2005/0138894 A1 | 6/2005 | Snell | |
| 2005/0138896 A1 | 6/2005 | Snell | |
| 2006/0032782 A1 * | 2/2006 | Suh et al. | 206/581 |

FOREIGN PATENT DOCUMENTS

| | | |
|---|---|---|
| WO | WO 02/17844 A2 * | 3/2002 |
| WO | WO 2005/009311 | 2/2005 |
| WO | WO 2005/055898 | 6/2005 |

OTHER PUBLICATIONS

"Baby Spa," Internet web page "http://www.giftcorpshop.com/IBS/SimpleCat/Product/asp/product-id/333042.html", Giftcorp, viewed and printed prior to Oct. 2004, 2 pages.

"Diaper Kits," Internet web page "http://www.safety-strap.org/diaperkits.html", SSC, viewed and printed prior to Oct. 2004, 2 pages.

"Dispense-A-Diaper" and "Diaper Kits", Internet web page "http://www.furniture-4kids.com/childrensfurniture/divemaststst.html", Internet Marketing Associates, viewed and printed prior to Oct. 2004, 2 pages.

"Lebrief Disposable Panties," Internet web page "http://www.dnaproductsonline.com/web/Product? product=2001", DNA Products, viewed and printed prior to Oct. 2004, 1 page.

"Pampers-Box," Internet web page "http://www.pampers-box.com/english/index.htm", The Procter & Gamble Company, viewed and printed prior to Oct. 2004, 1 page.

* cited by examiner

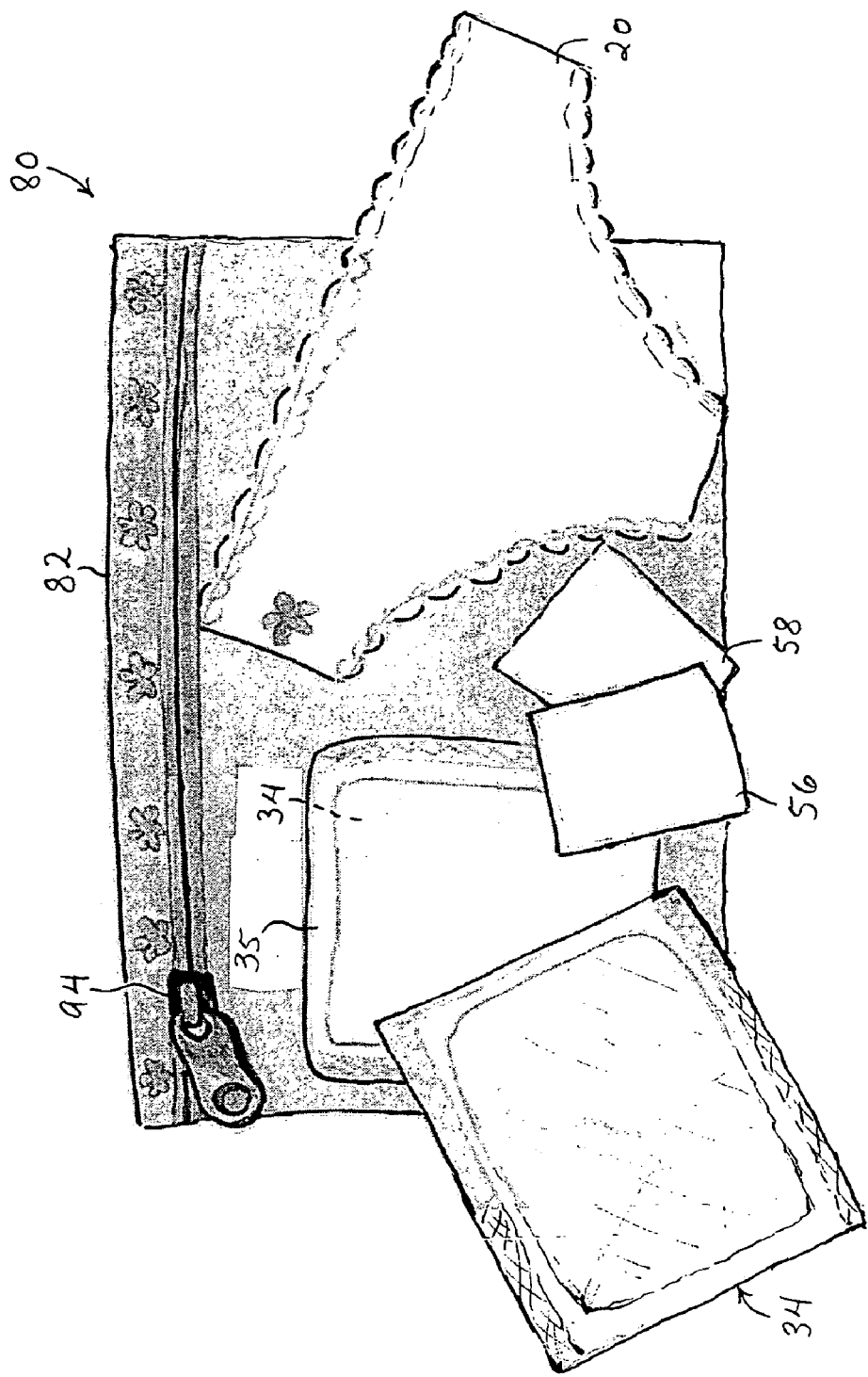

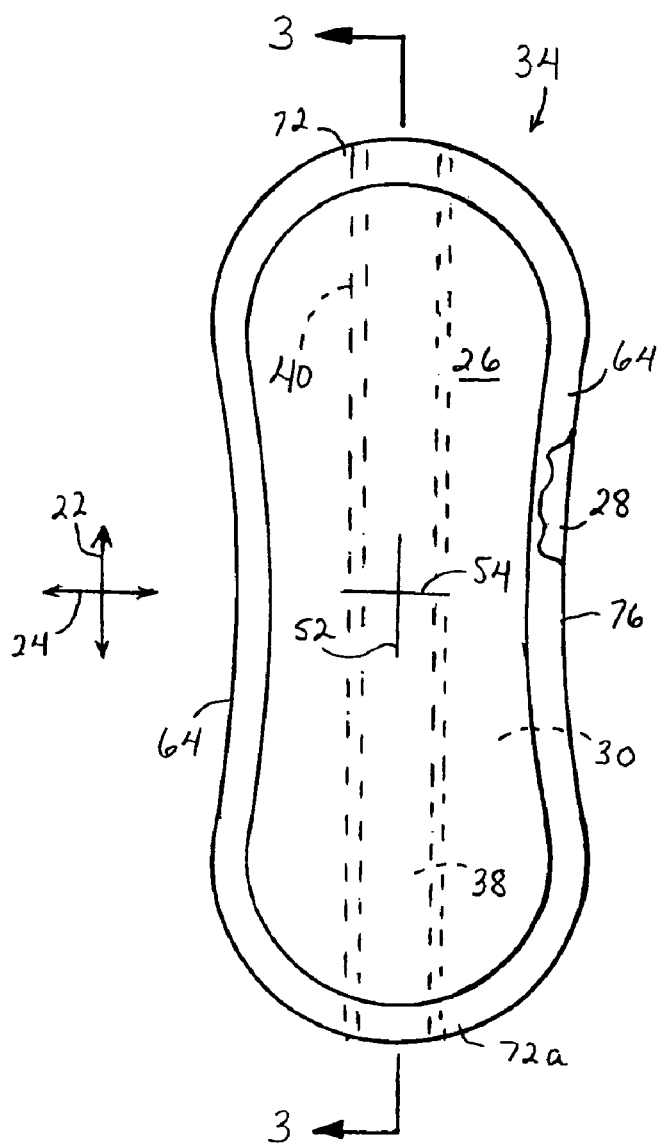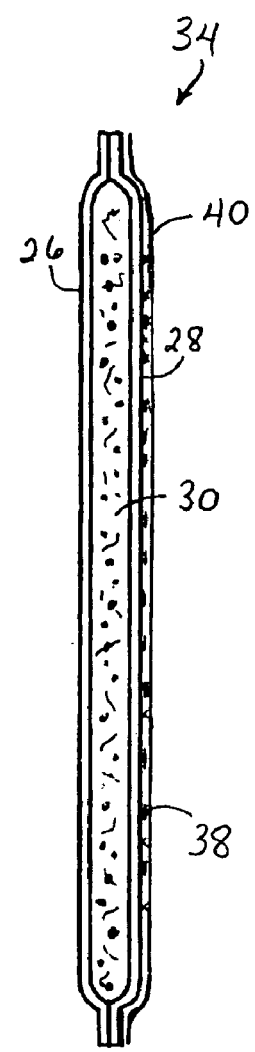
FIG. 2                    FIG. 3

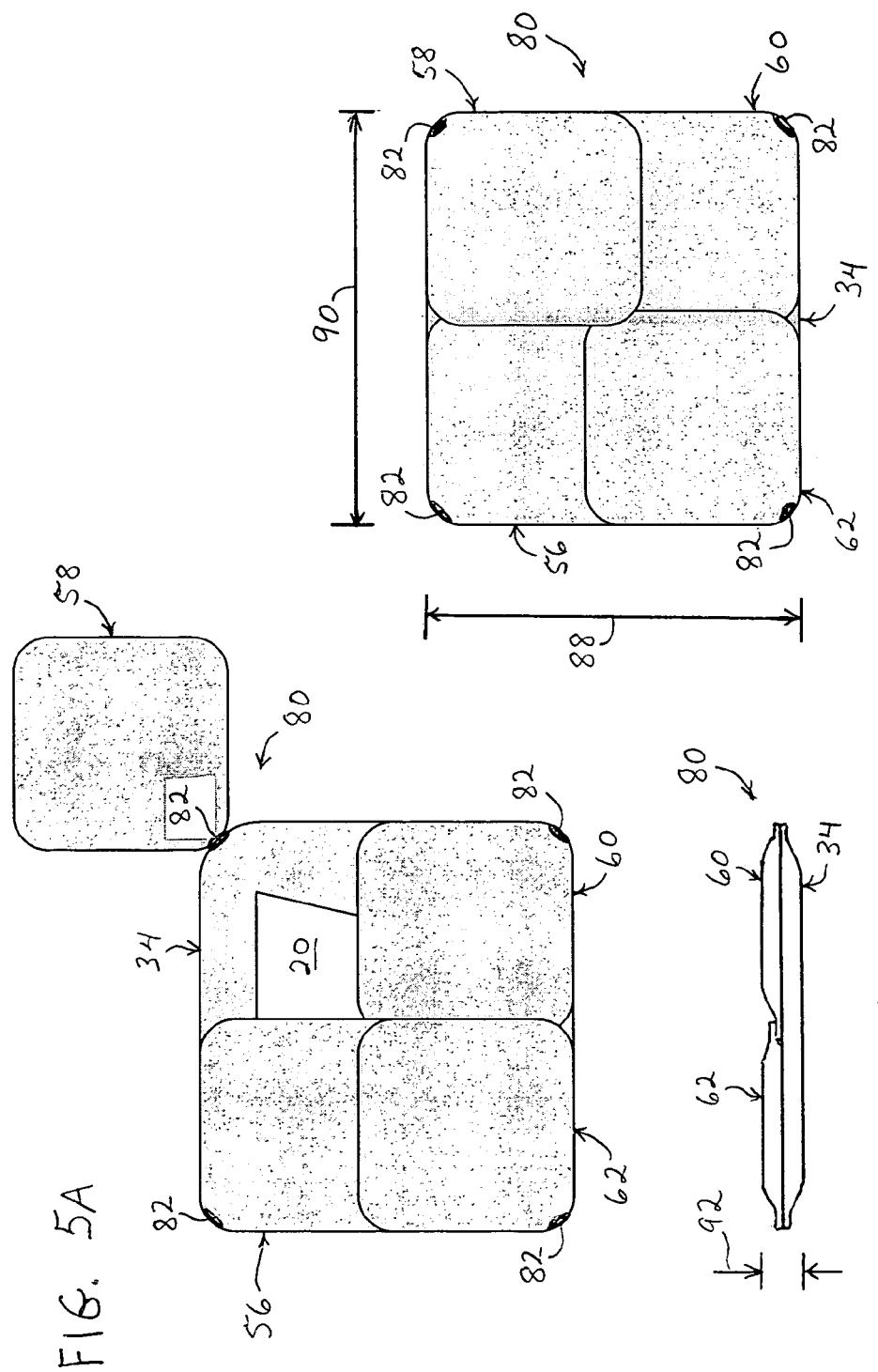

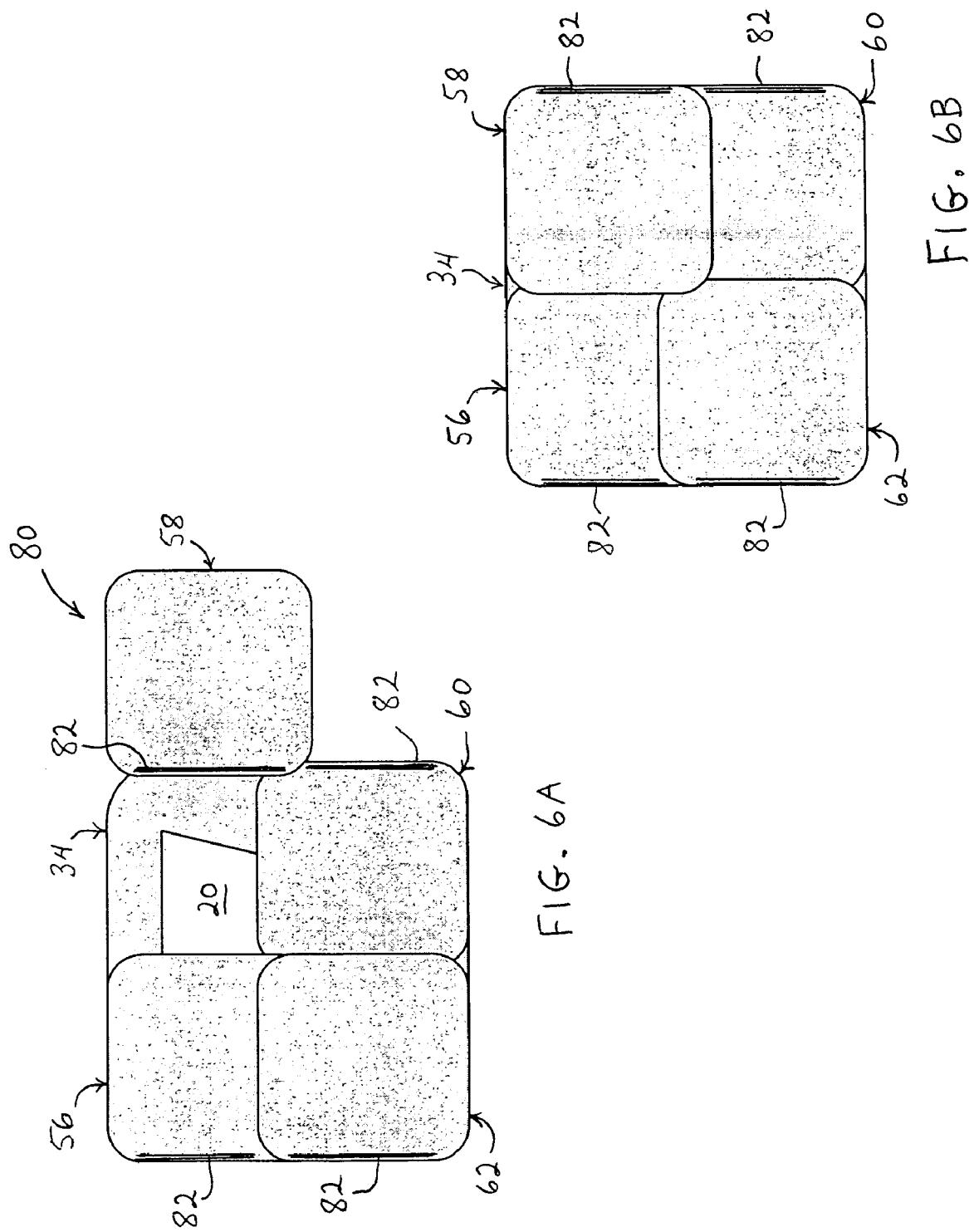

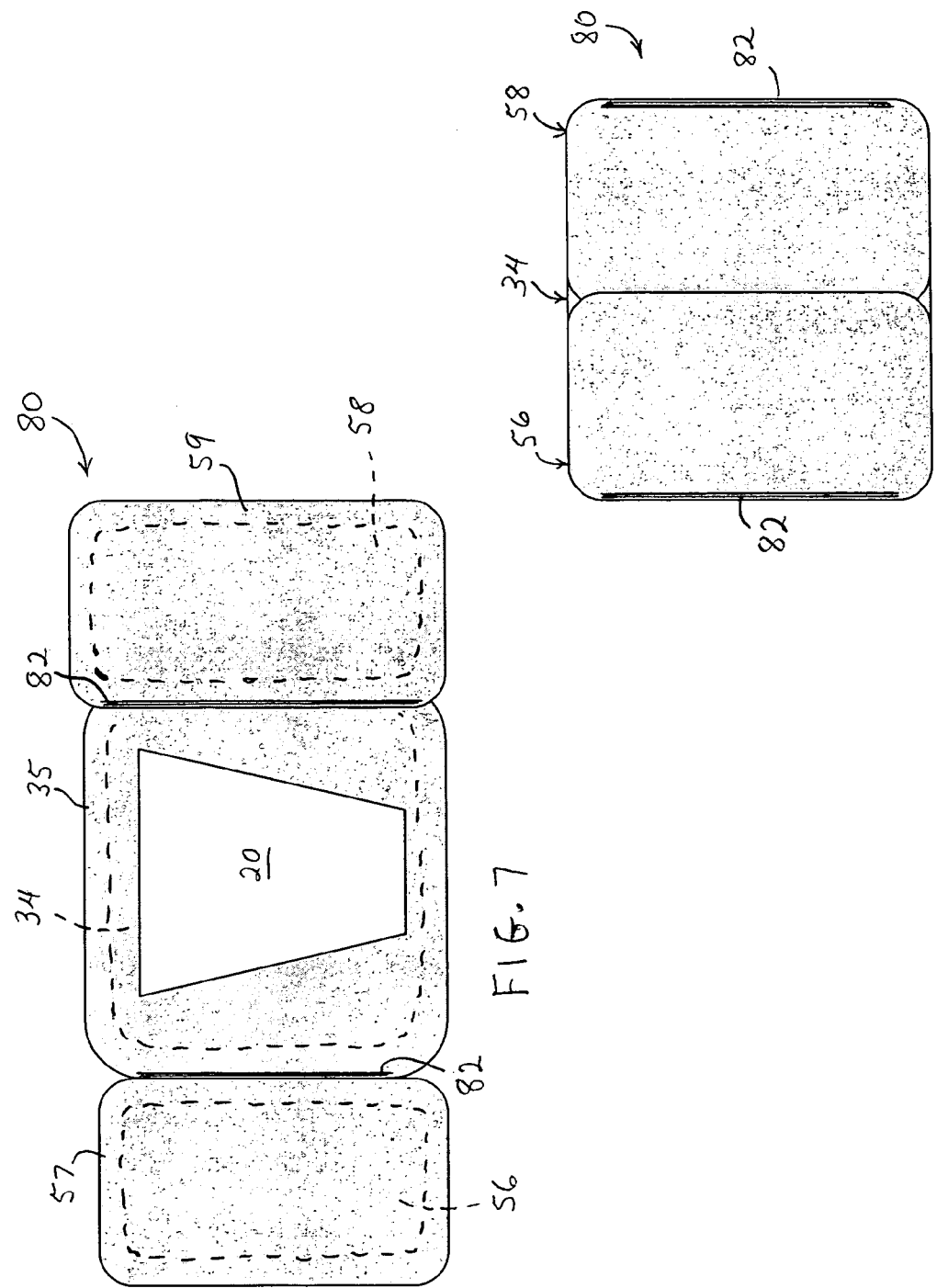

PERSONAL PRODUCT EMERGENCY KIT

FIELD OF THE INVENTION

The present invention relates to a kit for providing a distinctive system of personal care articles. More particularly, the present invention can provide a kit for providing a system of cooperating personal care articles which includes an absorbent article, such as feminine care products or adult incontinence products.

BACKGROUND OF THE INVENTION

Personal care articles, particularly personal care absorbent articles are well known in the art. The absorbent articles have been intended to absorb discharged body fluids, such as urine and/or menses. Such articles and products generally comprise a liquid permeable topsheet and a backsheet. Additionally, a fibrous mass or other absorbent body, which can absorb and hold the body fluids, is assembled between the topsheet and backsheet. In other arrangements, the personal care article may be a tampon article, and the tampon can comprise a liquid permeable topsheet and an absorbent body. Incontinence products have typically been employed to absorb liquids, such as urine. Feminine care articles have typically been employed to absorb urine, menses and other vaginal discharges. In particular arrangements, the feminine care articles have included a conventional garment-fastener for securing an individual article in a wearer's undergarment. In further arrangements, the articles have included wing portions which can help to hold the article in place at a selected location in a wearer's undergarment. In some arrangements, the wing portions have been integrally formed with one or more of the preexisting component layers that were employed to construct the article. In other arrangements, the wing portions have been separately provided components that are assembled and affixed to the final product. Conventional wing-fasteners have been employed to secure the wing portions in a desired configuration during ordinary use. The various garment-fasteners and wing-fasteners have included conventional fastening mechanisms, such as adhesive fasteners and mechanical fasteners, hook-and-loop fasteners and the like.

Other personal care articles have included wipes. The wipes may be wet or dry, and may include additional components. Such components have included fragrances, lotions, cleaning solutions, skin treatments, lubricants, medicines and the like, as well as combinations thereof. Additionally, conventional wipes have been assembled in combination with selected absorbent articles, such as diapers, feminine care pads and adult incontinence garments.

The personal care articles have also been contained in various conventional packaging systems. Individual articles may or may not have included wrappers, such as individual containment pouches composed of polymer films and/or nonwoven fabrics. Articles that contain liquids have been sealed in liquid-impermeable wrappers. Predetermined quantities of articles have also been grouped and contained in conventional packages, such as bags and/or cartons, and the selected packages could be opened to allow a desired extraction of the individual articles.

Conventional systems, however, have not sufficiently provided a desired convenience and easy access to a combination of individual, cooperating articles that may be desired when an initially employed, personal care absorbent article becomes soiled and needs replacement. The conventional packaging systems for the desired articles have also been excessively bulky and cumbersome to transport and use, and have not provided a desired combination of convenience and discretion. When encountering an emergency involving an unexpected soiling of clothing, the conventional systems and structures have not contained all of the components desired for use, or have included more components than needed.

As a result, there has been a continued need for an improved system of personal care articles that can more effectively provide a convenient access and packaging of a desired combination of cooperating personal care articles.

BRIEF DESCRIPTION OF THE INVENTION

Generally stated, the present invention can provide a personal care system which comprises a plurality of kit items and an assembly mechanism which holds the kit items together in a cooperating, combined unit. In a particular aspect, the kit items can include a substitute undergarment, and a supplemental absorbent article configured to cooperate with the substitute undergarment. In other aspects, the absorbent system can also include a first treatment-component configured to provide a first treatment-type, and at least a second treatment-component configured to provide a second treatment-type that differs from the first treatment-type.

By incorporating its various aspects, features and configurations, the system of the invention can more effectively meet the needs arising from an unexpected soiling of a user's clothing. The system of the invention can efficiently clean and/or deodorize bodily fluids from a wearer's clothing, conveniently provide a replacement or substitute undergarment, and provide an additional absorbent product. Additionally, the system of the invention can provide hygienic components for cleaning, drying, deodorizing or otherwise treating the user's skin, and can be efficiently sized to provide a small compact package that is easy to transport, use and store. In desired arrangements, the invention can include a combination of wipes for cleaning the user's body, and wipes for cleaning and/or deodorizing the user's clothing.

BRIEF DESCRIPTION OF THE DRAWINGS

The various features, aspects and advantages of the present invention will become better understood with reference to the following description, appended claims and accompanying drawings where:

FIG. 1 shows a representative system of personal care articles which includes selected kit items.

FIG. 2 shows a partially cut away, top plan view of a bodyside of a representative, supplemental absorbent article that can be employed with the personal care system of the invention.

FIG. 3 shows a view of a representative, longitudinal cross-section through a supplemental personal care article that can be employed with the system of the invention.

FIG. 5A shows a schematic view of the personal care system of FIG. 5 in a partially open condition.

FIG. 5B shows a schematic view of the personal care system of FIG. 5 in a fully closed condition.

FIG. 5C shows a representative, schematic side view of the fully closed condition of the personal care system in FIG. 5B.

FIG. 6A shows a schematic view of the configuration of the personal care system of FIG. 6 in a partially open condition.

FIG. 6B shows a schematic view of the personal care system of FIG. 6 in a completely closed condition.

FIG. 7 shows a schematic view of another representative configuration of a personal care system in a fully open condition.

FIG. 7A shows a schematic view of the configuration of the personal care system of FIG. 7 in a completely closed condition.

DETAILED DESCRIPTION OF THE INVENTION

Figure 4:
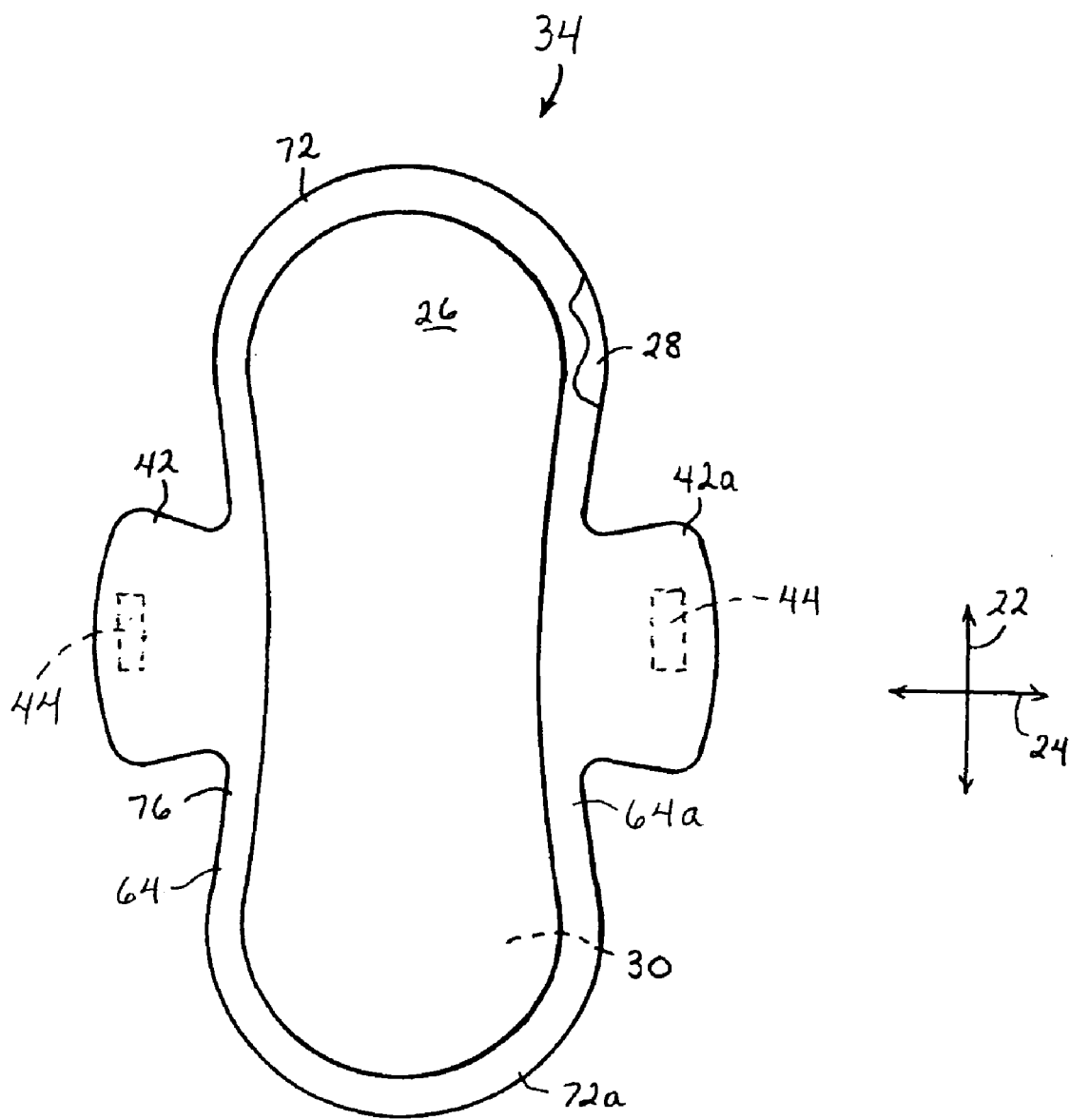
FIG. 4 shows a partially cut away, top plan view of a garment-side of a representative, supplemental personal care article having a pair of wing-panels, where the wing-panels are arranged in a laterally-extended position.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the adsorbent material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, a substantially liquid impervious backsheet operatively joined or otherwise operatively connected to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof, can operate to provide a body-facing surface and a garment-facing surface. As used herein, "body-facing surface" means that surface of the article or component which is intended to be disposed toward or placed adjacent to the body of the wearer during ordinary use, while the "outward surface" or "outward-facing surface" is on the opposite side, and is intended to be disposed to face away from the wearer's body during ordinary use. The outward surface may be arranged to face toward or placed adjacent to the wearer's undergarments when the absorbent article is worn.

Many users or consumers lead active lives, with activities that include going to a job, visiting friends, participating in social events, participating in sporting events, enjoying the arts, traveling and the like. In various situations, an unexpected sneeze or cough, or a high level of stress or anxiety can cause urine loss or other wetting of a persons clothing. The leaking of an absorbent product during the person's activities can be a very unpleasant event, which causes anxiety or limits the scope or enjoyment of the activities. It has been found that the ordinary combination of an absorbent pad product with a wet wipe or a dry wipe, has often been insufficient to meet the needs of users in a social or away from home situation. Should the users experience leakage onto their reusable clothing, they would need to change their underwear and clean and/or deodorize any outer clothing that was being worn. These conventional packages of absorbent pad products and wet or dry wipes have not adequately addressed the situation. The user's underwear has remained wet against the user's skin and has caused undesired irritation. Also, the user's items of clothing have undesirably developed embarrassing malodors. To address the shortcomings of prior, conventional systems, the present invention can advantageously provide a distinctive system of personal care items that will more effectively meet the user's needs should the undesired leakage occur.

With reference to FIG. 1, the present invention provides a personal care system 80 which comprises a plurality of kit items, and an assembly mechanism 82 which holds the kit items together in a cooperating, combined unit. In a particular aspect, the kit items can include a substitute undergarment 20, and a supplemental absorbent article 34 which is configured to cooperate with the substitute undergarment 20. In other aspects, the absorbent system can also include a first treatment-component 56 which is configured to provide a first treatment-type, and at least a second treatment-component 58 which is configured to provide a second treatment-type that differs from the first treatment-type. Optionally, the personal care system may be configured to operatively provide a bag or other container that can be employed to carry any soiled items.

By incorporating its various aspects, features and configurations (alone or in desired combinations), the present invention can provide a convenient and easy-to-use personal care system which includes a distinctive combination of cooperating items that can be utilized in situations where a user's reusable, outer garment or garments have been unexpectedly soiled by discharges of body liquids. Such reusable outer-garments are ordinarily intended to be washed or otherwise cleaned for reuse and further wear. For example, the system of the invention can more efficiently and more conveniently handle and accommodate at least one change of underwear necessitated by an unexpected discharge of body fluid(s). Additionally, the personal care system can more effectively provide a combination of emergency kit items that can be employed to clean up or otherwise treat the user's skin and reusable outer-garments. The kit items can, for example, be employed to clean and dry the person's skin, neutralize odor in the person's clothing, and provide an undergarment article for temporary use. Additionally, the personal care system can be conveniently carried in a purse, backpack or pocket and can be immediately available in times of emergency.

In a particular feature, the kit items can include at least one substitute undergarment. The substitute undergarment can, for example, be a disposable undergarment or other limited-use undergarment, and the undergarment may include a woven fabric, a knitted fabric, a nonwoven fabric or the like, as well as combinations thereof. Desirably the substitute undergarment can be a disposable panty, and in desired configurations, the substitute undergarment can be soft and stretchy. In another feature, the kit items can include a supplemental absorbent article, such as pad, pantiliner, garment shield or the like. A further feature can provide a selected plurality of treatment components, such as a wet wipe, dry wipe, powder wipe or the like. The treatment component may include a wipe for clothing, such as a cleaning wipe, deodorizing wipe, scented wipe. The wipes may be hypo-allergenic, may be flushable and may provide a freshening moist wipe, soft-powder drying wipe, and/or a wipe that can clean and freshen a user's conventional outer clothing. Additionally, the system can optionally be configured to operatively provide a holding device that can be employed to store any item of soiled clothing for transport and later cleaning. The holding device may be integrally formed with another component of the personal care system 80, or may include a separately provided container or other separately provided mechanism. The holding device may, for example, be employed to hold a soiled, reusable undergarment, such as a panty, brief or set of underpants. Accordingly, the personal care system 80 can provide a compact, light-weight emergency kit that can be conveniently and discreetly carried during long or short trips.

The substitute undergarment 20 may be any suitable undergarment, such as a panty, a set of underpants, a set of briefs or the like. The substitute undergarment may be a reusable undergarment, a limited use undergarment or a disposable undergarment, as desired. Substitute undergarments are conventional and well known in the art. For example, conventional substitute undergarments are described in detail in: U.S. Pat. No. 3,594,820 entitled DISPOSABLE PANTY by Marion McCurry which was issued Jul. 27, 1971; U.S. Pat. No. 3,636,953 entitled DISPOSABLE PANTY WITH IMPROVED CROTCH CONSTRUCTION by Joseph Benevento which was issued Jan. 25, 1972; U.S. Pat. No. 4,698,855 entitled DISPOSABLE TRY-ON'S by Josephine Hicks which was issued Oct. 13, 1987; U.S. Pat. No. 4,883,481 entitled ADJUSTABLE DISPOSABLE PANTY by JoAnn Blanchard which was issued Nov. 28, 1989; U.S. Pat. No. 6,367,089 B2 entitled DISPOSABLE MENSTRUAL PANTY by Paul VanGompel et al. which was issued Apr. 9, 2002; and U.S. Patent Application Publication entitled DISPOSABLE PANTIES FOR FEMALES by Bernice McQueen which was published Feb. 12, 2004. The entire disclosures of these documents are incorporated herein by reference in a manner that is consistent herewith. Other substitute undergarments are commercially available from vendors. For example, ABENA ABRI-PANTS and ABRI-LEAF pants are available from Saekko-Bambo Group, Denmark.

The disposable panty or other substitute undergarment 20 can provide an important component of the system, which targets a true crisis element in a situation where the user may need to change quickly and discreetly when away from home. In particular, the substitute undergarment can provides an item of temporary clothing until the user has the time or opportunity to obtain an appropriate change of clothing. The substitute undergarment 20 may or may not include an absorbent component that provides a significant amount of absorbent capacity. In particular arrangements, the substitute undergarment may include an absorbent component having a minimal or relatively small amount of absorbent capacity. The substitute undergarment may have any suitable configuration, including particular designs or styles for female or male users, and may optionally include belts or straps that fasten to the wearer or to the cooperating supplemental absorbent article 34. The substitute undergarment 20 can, for example, be an article of disposable underwear such as a panty, brief, pair of shorts, shield or the like. The substitute undergarment may or may not include a retention component for absorbing and holding bodily liquids, and may not include belts straps or other fastening components. Additionally, the fastening components may be releasable and refastenable.

Any suitable supplemental absorbent article 34 can be configured for inclusion in the present invention. In desired arrangements, the supplemental absorbent article can be an adult incontinence article or a feminine care article. The feminine care article can, for example, be a feminine care pad, pantiliner, tampon or napkin. With reference to FIGS. 2 and 3, the article has an appointed bodyside surface, an appointed garment-side surface, a lengthwise longitudinal-direction 22, a lateral cross-direction 24, a pair of longitudinally-extending, laterally-opposed side edge regions 64, and an intermediate portion 76 which is interposed between a pair of longitudinally opposed end portions 72 (72, 72a). The supplemental absorbent article also has a longitudinally extending centerline 52 and a laterally extending centerline 54. As representatively shown, the longitudinal dimension of the article is relatively larger than the lateral dimension of the article. In particular configurations, the supplemental absorbent article 34 can include a baffle or backsheet 28, and a liquid-permeable cover or topsheet 26 which is operatively connected in a facing relation with the backsheet. In particular configurations, the supplemental absorbent article may further include an absorbent body structure 30 which is operatively positioned and sandwiched between the backsheet 28 and topsheet 26. As representatively shown, peripheries of the topsheet and backsheet may extend beyond the periphery of the absorbent body, and may be substantially entirely coterminous. Optionally, the peripheries of the topsheet 26 and the backsheet 28 may be partially or entirely non-coterminous, and the peripheries of the topsheet and backsheet may not extend beyond the periphery of the absorbent body.

In a desired feature, the supplemental absorbent article 34 can also include at least one pair of wing-panels 42 (e.g. FIG. 4). A first wing-panel 42 can be attached to a first side edge region 64 in the intermediate portion 76 of the article 34, and a second wing-panel 42a can be attached to a second side edge region 64a in the intermediate portion 76 of the article 34. Each wing-panel 42 (42, 42a) can be configured to wrap about an undergarment of a wearer. A panel fastener 44 can be joined or otherwise operatively connected to each wing-panel 42, and each panel fastener 44 can be configured to operatively secure its corresponding wing-panel 42 about the undergarment of the wearer during ordinary use. Each wing-panel 42 can include a panel base section and a panel free-end region, and each panel base section can be operatively joined or otherwise operatively connected to its corresponding side edge region 64 of the supplemental absorbent article 34. Each panel free-end region can extend from its corresponding panel base section, and can be configured to operatively wrap around an appointed region of the wearer's undergarment. For example, the free-end regions of the wing-panels can be wrapped about a crotch region of the wearer's undergarment.

The cover or topsheet 26 may include any material that can be configured to provide the topsheet with an operative level of liquid-permeability. The topsheet may be constructed with one or more layers of suitable materials, and may be a composite material. For example, the topsheet layer can include a woven fabric, a nonwoven fabric, a polymer film, a film-fabric laminate or the like, as well as combinations thereof. Examples of a nonwoven fabric include, spunbond fabric, meltblown fabric, coform fabric, a carded web, a bonded-carded-web, a bicomponent spunbond fabric or the like as well as combinations thereof. For example, the topsheet layer can include a woven fabric, a nonwoven fabric, a polymeric film that has been configured to be operatively liquid-permeable, or the like, as well as combinations thereof. Other examples of suitable materials for constructing the topsheet layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A more particular example of a suitable topsheet layer material can include a bonded-carded-web composed of polypropylene and polyethylene, such as has been used as a topsheet stock for KOTEX brand pantiliners. Suitable topsheet materials have been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the topsheet layer 26 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, that are present or formed in the topsheet layer. The apertures or other openings can help increase the rate at which bodily liquids can move through the thickness of the topsheet layer and penetrate into the other components of the article (e.g. into the absorbent structure 30). The selected arrangement of liquid-permeability is desirably present at least on an operative portion of the topsheet layer that is appointed for placement on the body-side of the article. The topsheet layer 26 can provide comfort and conformability, and can function to direct bodily exudates away from the body and toward the absorbent body structure 30. In a desired feature, the topsheet layer 26 can be configured to retain little or no liquid in its structure, and can be configured to provide a relatively comfortable and non-irritating surface next to the body-tissues of a female wearer. The topsheet layer 26 can be constructed of any material which is also easily penetrated by bodily fluids that contact the surface of the topsheet layer.

The topsheet 26 can also have at least a portion of its bodyside surface treated with a surfactant to render the topsheet more hydrophilic. The surfactant can permit arriving bodily liquids to more readily penetrate the topsheet layer. The surfactant may also diminish the likelihood that the arriving bodily fluids, such as menstrual fluid, will flow off the topsheet layer rather than penetrate through the topsheet layer into other components of the article (e.g. into the absorbent body structure). In a particular configuration, the surfactant can be substantially evenly distributed across at least a portion of the upper, bodyside surface of the topsheet 26 that overlays the upper, bodyside surface of the absorbent.

The topsheet 26 may be maintained in secured relation with the backsheet 28 and/or the absorbent structure 30 by bonding all or a portion of the adjacent surfaces to one another. A variety of bonding techniques known to one of skill in the art may be utilized to achieve any such secured relation. Examples of such techniques include, but are not limited to, the application of adhesives in a variety of patterns between the two adjoining surfaces, entangling at least portions of the adjacent surface of the absorbent with portions of the adjacent surface of the topsheet, or fusing at least portions of the adjacent surface of the topsheet to portions of the adjacent surface of the backsheet and/or absorbent.

The topsheet 26 extends over the upper, bodyside surface of the article, and typically extends over any employed absorbent structure to provide a bodyside liner. The topsheet can optionally extend around the article to partially or entirely, surround or enclose the absorbent structure. Alternatively, the topsheet 26 and the backsheet 28 can have peripheral margins which extend outwardly beyond the terminal, peripheral edges of the absorbent structure 30, and the extending margins can be operatively joined or otherwise operatively connected together to partially or entirely, surround or enclose the absorbent structure.

The baffle or backsheet 28 may include a layer constructed of any operative material, and may or may not be configured to be liquid-permeable. In a particular configuration, the backsheet 28 may be configured to provide an operatively liquid-impermeable layer. The backsheet may, for example, include a polymeric film, a woven fabric, a nonwoven fabric or the like, as well as combinations or composites thereof. For example, the backsheet may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the backsheet 28 can operatively permit a sufficient passage of air and moisture vapor out of the article, particularly out of an absorbent (e.g. the absorbent structure 30) while blocking the passage of bodily liquids. An example of a suitable backsheet material can include a breathable, microporous film, such as a HANJIN Breathable backsheet available from Hanjin Printing, Hanjin P&C Company Limited, a business having offices located in Sahvon-li.Jungan-mvu.Kongiu-City, Chung cheong nam-do, Republic of South Korea. The backsheet material is a breathable film, which is white in color, dimple embossed, and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed cell polyolefin foam. For example, a closed cell polyethylene foam may be employed. Still another example of a backsheet material would be a material that is similar to a polyethylene film which is used on commercially sold KOTEX brand pantiliners. Suitable film materials have been obtainable from Pliant Corporation, a business having offices located in Schaumburg, Ill., USA.

The structure of any employed absorbent body 30 can be operatively configured to provide a desired level of absorbency or storage capacity. More particularly, the absorbent body can be configured to hold a liquid, such as urine, menses, other complex liquids or the like, as well as combinations thereof. As representatively shown, the absorbent body can include a matrix of absorbent fibers and/or absorbent particulate material, and the absorbent fiber can include natural and/or synthetic fiber.

Any employed absorbent structure 30 may also include superabsorbent material. Superabsorbent materials suitable for use in the present invention are known to those skilled in the art, and may be in any operative form, such as layers, fibers, particles or the like, as well as combinations thereof. Generally stated, the water-swellable, generally water-insoluble, hydrogel-forming polymeric absorbent material (superabsorbent) is capable of absorbing at least about 10, desirably about 20, and possibly about 100 times or more its weight in water. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as The Dow Chemical Company, Hoechst Celanese Corporation, Allied Colloid Inc., and Stockhausen, Inc.

The absorbent body 30 can be substantially unitary with a non-uniform structure or a generally uniform structure. Alternatively, the absorbent body may include a composite structure having a selected plurality of strata or layers. For example, the absorbent body structure may include an intake layer, a distribution layer, a transfer layer, a transfer-delay layer, a shaping layer, a retention layer or the like, as well as combinations thereof. The various strata and/or layers may be stacked, distributed or otherwise arranged in any operative sequence or configuration.

The absorbent body 30 may be an absorbent composite which may, for example, include either or both of an intake layer, and an absorbent retention layer. In a particular arrangement, the absorbent body can include an absorbent retention layer which is positioned between the topsheet 26 and the backsheet 28. Additionally, the absorbent body can include an intake layer which is positioned between topsheet 26 and the retention layer. The absorbent body can further include one or more additional layers positioned between the topsheet 26 and backsheet 28. The various individual layers may be separately provided layer-components, may be integrally formed together, or may be provided as any operative combination of separately-provided and integrally-formed layers.

The intake layer can provide a desired intake of liquid and distribution of the liquid. The intake layer may include natural fibers (e.g. cellulose fibers), synthetic fibers, superabsorbent materials, a woven fabric; a nonwoven fabric; a wet-laid fibrous web; a substantially unbonded airlaid fibrous web; an operatively bonded, stabilized-airlaid fibrous web; a multifunctional stabilized-airlaid fibrous web; a film material; a foam material or the like; as well as combinations thereof.

The retention layer can provide a desired, absorbent retention or storage function, and may provide a selected shaping of the absorbent article. The retention layer may include natural fibers (e.g. woodpulp fluff or other cellulosic fibers), synthetic fibers, superabsorbent materials, a woven fabric; a nonwoven fabric; a wet-laid fibrous web; a substantially unbonded airlaid fibrous web; an operatively bonded, stabilized-airlaid fibrous web; a multifunctional stabilized-airlaid fibrous web; a film material; a foam material or the like; as well as combinations thereof.

In particular arrangements, the intake and/or retention layer can be a thermally-bonded, stabilized-airlaid fibrous web. The stabilized-airlaid web can have a basis weight of about 100–300 $g/m^2$, and a density of about 0.06–0.08 $grams/cm^3$. Suitable stabilized-airlaid webs are available from Concert Fabrication, a business having offices located in Gatineaux, Quebec, Canada.

Additionally, the absorbent article can include any desired pattern or array of embossments. In particular aspects, the embossments may be formed on the bodyside surface of the article. Desired arrangements can include an absorbent body structure that has embossment regions formed on at least its bodyside surface. Similarly, the other employed components of the article can also include corresponding embossed regions.

The supplemental absorbent article 34 may include a system of side "wings" or wing-panel portions 42, which are positioned along both lateral side regions 64 of the article, as representatively shown in FIG. 4. The wing-panels can be separately provided members that are subsequently attached or otherwise operatively joined or operatively connected to the intermediate portion of the article 34. The separately provided wing-panel member can be operatively attached to at least one of the backsheet 28 and/or topsheet 26. In an alternative arrangement, each wing-panel 42 can be provided by an integrally-formed side portion of the article 34. The wing-panels may be integrally formed from another component of the article, such as the topsheet and/or the backsheet, and operatively joined or otherwise operatively connected to appointed sections of the article side regions 64 along the intermediate portion of the article.

In a particular configuration, each wing-panel 42 can include an integrally-formed side portion of the backsheet 28 which extends laterally past a corresponding, terminal side edge of the absorbent body 30. In another arrangement, each wing-panel 42 can include an integrally-formed side portion of the topsheet 26 which extends laterally past a corresponding, terminal side edge of the absorbent body. Still a further arrangement can have a configuration wherein each wing-panel 42 includes a panel composite. The panel composite can, for example, include an integrally-formed side portion of the backsheet 28 which extends laterally past a corresponding, terminal side edge of the absorbent body, and an integrally-formed cooperating, side portion of the topsheet 26 which extends laterally past the corresponding, terminal side edge of the absorbent body. The cooperating, side portion of the topsheet 26 is positioned in facing relation with the integrally-formed side portion of the backsheet 28.

In the cooperating pair of wing-panels, the first wing-panel 42 can be attached or otherwise operatively joined or operatively connected to a first side edge region 64 in the intermediate portion 76 of the article 34, and the second wing-panel 42a can be attached to a second side edge region 64a in the intermediate portion of the article. Each wing-panel 42 (42, 42a) can be configured to operatively wrap about a selected section of a wearer's undergarment.

The wing-panels can have an appointed storage position in which the wing-panels 42 are directed generally inwardly toward the longitudinally-extending centerline 52. The wing-panel that is connected to extend from one side margin may have sufficient cross-directional length to extend and continue past the centerline 52 to approach the laterally opposite side margin of the article. The storage position of the wing-panels can ordinarily represent an arrangement observed when the article is first removed from its wrapper or other packaging. Prior to placing the article into a bodyside of an undergarment prior to use, the wing-panels 42 can be selectively arranged to extend laterally from the side regions 64 of the article intermediate portion. After placing the article in the undergarment, the wing-panels 42 can be operatively wrapped and secured in an in-use position around the side edges of the undergarment crotch portion to help hold the article in place. Typically, the wing-panels are configured to secure the article to a crotch portion of the wearer's undergarment.

The wing-panel portions 42 can have any operative construction, and can include a layer of any operative material. Additionally, each wing-panel can comprise a laminate or other composite material. For example, the wing-panels may include a spunbond fabric material, a bi-component spun-bond material, a necked spunbond material, a neck-stretched-bonded-laminate (NBL) material, a meltblown fabric material, a bonded carded web, a thermal bonded carded web, a through-air bonded carded web or the like, as well as combinations thereof.

The wing-panel materials can be substantially non-stretchable or may be stretchable. The wing-panel material may also be capable of providing a selected amount of nonelastomeric extension, or a selected amount of elastomeric stretch and retraction, as desired. In particular configurations, the wing-panel material can exhibit a maximum stretch elongation value of up to about 300%, or more. In other configurations, the wing-panel material can exhibit a minimum stretch elongation value of 50%. In other features, the wing-panel material can have a basis weight which is within the range of about 0.5–3 ounces per square yard (about 17–102 $g/m^2$). By employing such wing-panel materials, the wing-panel can help provide desired fit characteristics, and can help provide improved leak protection.

Each wing-panel 42 can include a panel-fastener component 44 which is operatively joined or otherwise operatively connected to a major facing surface of the associated wing-panel. Such major surface is typically appointed to engage and become operatively attached to an outward-facing surface of the wearer's undergarment. The panel-fastener 44 can include any operative fastener component, such as a component of an interengaging mechanical fastener, an adhesive fastener, a cohesive fastener, a magnetic fastener, an electromechanical fastener or the like, as well as combinations thereof. The mechanical fastener component may, for example, include a suitable hook component, such as a J-hook, mushroom-head hook, flat-top nail-head hook, a palm-tree hook, a multiple-J hook or the like, as well as combinations thereof. Optionally, the mechanical fastener component may, for example, include a suitable loop component. The loop component may, for example, include a knit fabric, a woven fabric, a nonwoven fabric or the like, as well as combinations thereof.

Each wing-panel 42 can include a panel base section and a panel free-end region. Each panel base section can be operatively joined or otherwise operatively connected to its corresponding side edge region 64 of the article 34, and each panel free-end region can extend from its corresponding panel base section. The free-end region can be further configured to operatively wrap around an appointed region of the wearer's undergarment. For example, the free-end regions of the wing-panels can be wrapped about a crotch region of the wearer's undergarment.

With reference to FIGS. 2 and 3, a selected configuration of a garment-fastener or other garment-attachment mechanism 38 may be operatively distributed and joined or otherwise operatively connected onto the garment-side surface of the article 34 to help secure the article to the undergarment. The garment-fastener can include any operative fastener mechanism, such as a component of an interengaging mechanical fastener, an adhesive fastener, a cohesive fastener, a magnetic fastener, and electromechanical fastener or the like, as well as combinations thereof. Additionally, the garment-fastener may be arranged on any operative pattern, such as one or more strip regions that are distributed onto the garment-side of the article. In a particular arrangement, for example, an adhesive garment-fastener can be operatively distributed over the garment-side of the backsheet, and one or more layers or sheets of release material 40 can be removably placed over the garment adhesive during storage prior to use. In desired arrangements, at least a significant portion of the garment-attachment mechanism 38 can be generally aligned or otherwise located along the longitudinal centerline 52 of the article.

In a further aspect, the supplemental absorbent article 34 can include a corresponding article packet 35 which has been configured to hold the supplemental absorbent article. The packet 35 may be provided by a pouch, envelope, wrapper or the like, and can be constructed to operatively hold and store the supplemental article 34.

In a particular aspect of the invention, the system can include the first treatment-component 56 which is configured to provide a first treatment-type. In another aspect, at least a second treatment-component 58 can be configured to provide a second treatment-component type that differs from the first treatment-type. In desired configurations, the first treatment-component 56 can be provided by a wipe. Similarly, the second treatment-component 58 may be provided by another operative wipe.

Figure 5:
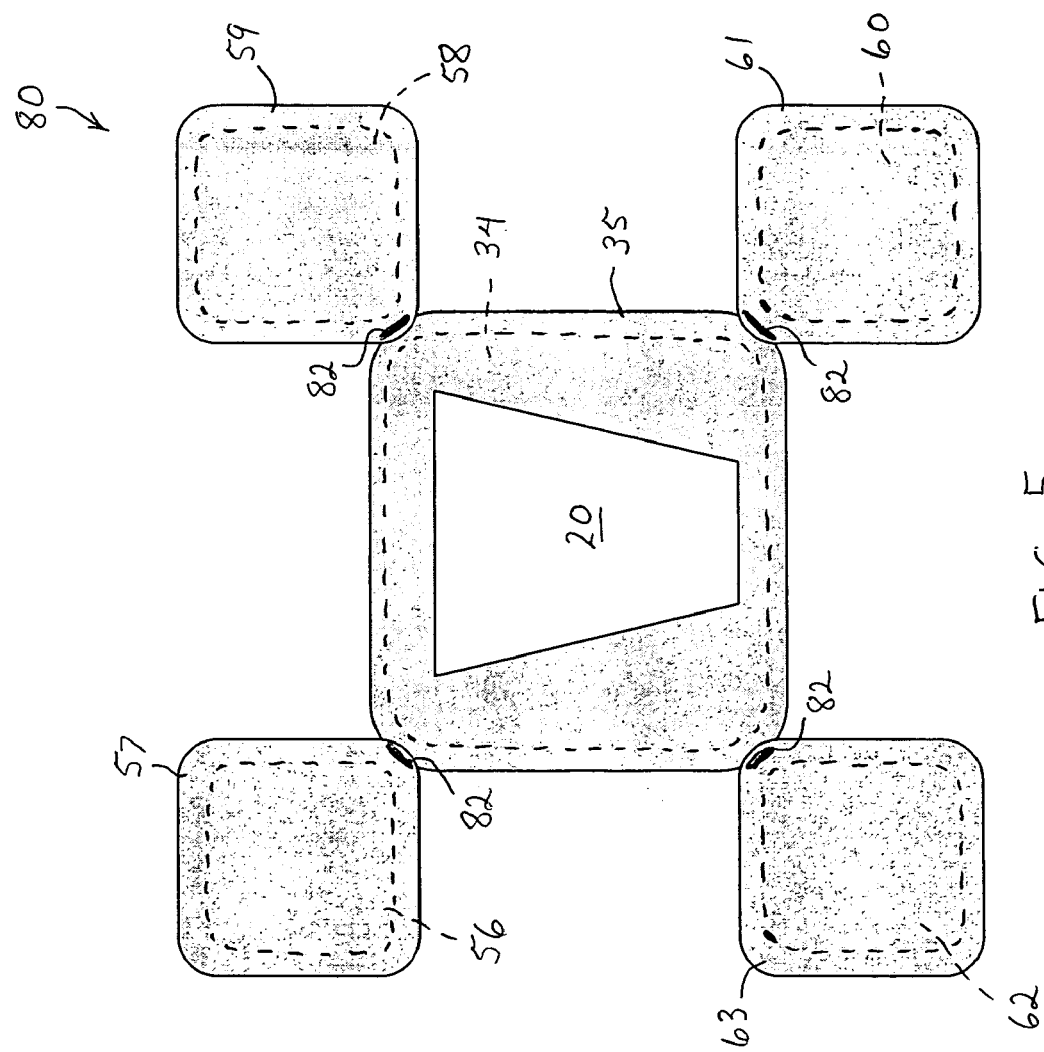
FIG. 5 shows a schematic view of a representative configuration of a personal care system in a fully open condition.
Figure 6:
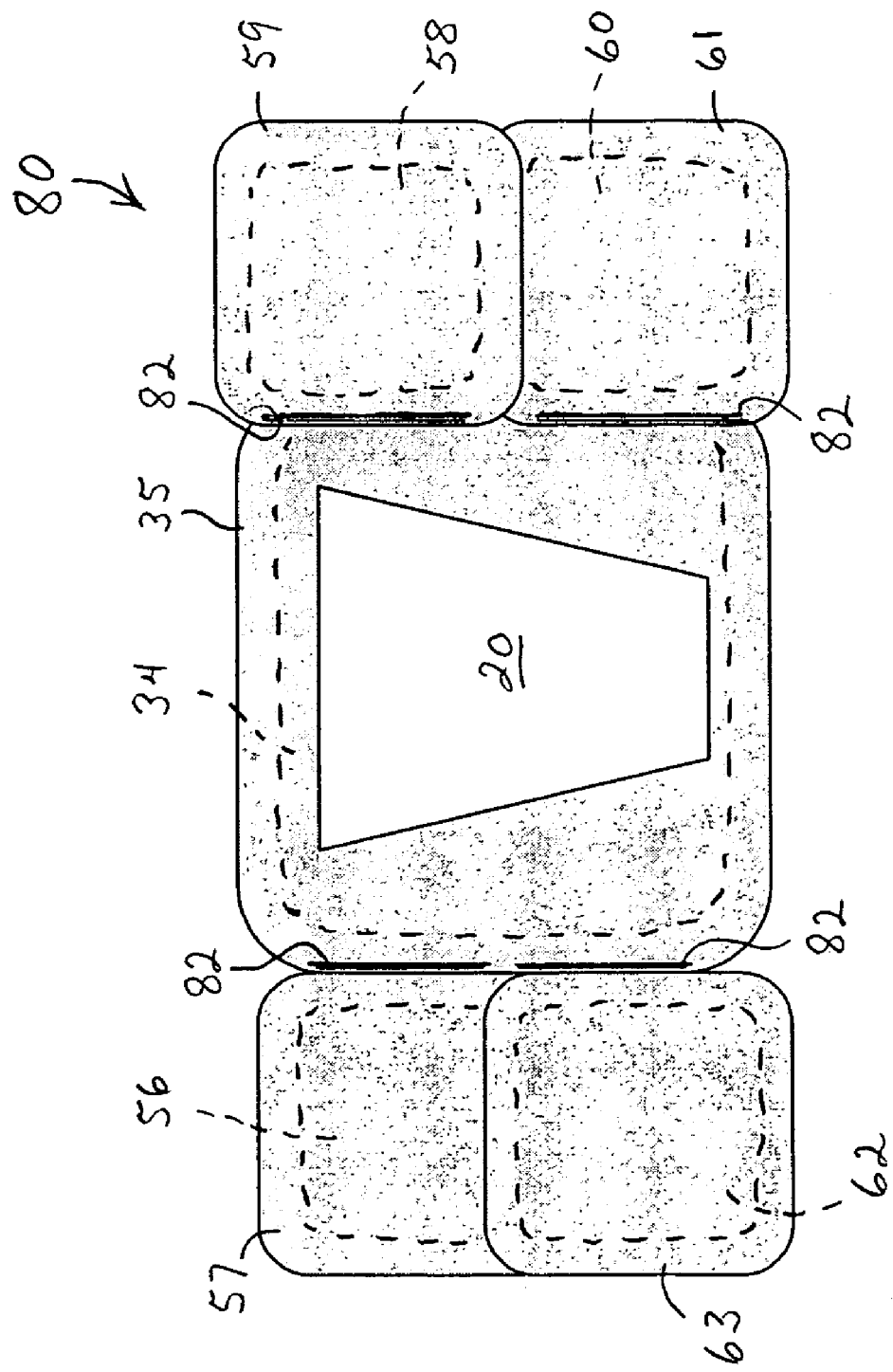
FIG. 6 shows a schematic view of another representative configuration of a personal care system in a fully open condition.

As representatively shown in FIGS. 5 through 6B, the kit items can further include a third treatment-component configured to provide a third treatment-type that differs from the first and second treatment-types. In a desired aspect, the third treatment-component 60 can include a third wipe. In still other configurations, the kit items can further include a fourth treatment-component configured to provide a fourth treatment-type that differs from the first, second and third treatment-types. In a desired arrangement, the fourth treatment-component can have the configuration of a fourth wipe. It should be readily appreciated that additional treatment-components may optionally be included in the personal care system 80, as desired, to provide further, different treatment-types. In the various configurations of the invention, the selected treatment-types differ in kind, not merely in degree.

In the various configurations of the invention, the selected treatment-component can alternatively be provided by one or more components or applicator devices. Such components or applicator devices can include fabric wipes, polymer sheet wipes, sponges, tissues, swabs, dissolvable sheets, applicator tapes, shakers, apertured containers for dispensing a gel, liquid, lotion, powder or the like, sprinklers, sprayers, injectors or other similar applicators, as well as combinations thereof.

In the various configurations of the invention, each selected treatment-component can include a dry-component or a wet-component. For example, the personal care system can include at least one wet wipe and at least one dry wipe. In a particular feature, the selected treatment-component may provide a desired cleaning and/or drying of the user's skin and/or body hair. For example, a selected treatment-component can be configured to deliver a cleansing solution, and another treatment-component can be configured to provide an absorbent device that can soak up liquids from the user's body or clothing.

In a further feature, the selected treatment-component can be configured to clean or otherwise treat a selected fabric, such as a woven or knit fabric. For example, the wipe or other employed treatment-component can be configured to clean bodily waste material from a selected reusable fabric, such as the fabric of a reusable garment. Accordingly, the selected treatment-component can be configured to operatively clean bodily waste material from a reusable undergarment or a reusable, outer-garment, such as a dress, a skirt, a pair of pants or the like. As a result, the personal care system can enhance the user's appearance, and help to limit, mask, neutralize or eliminate odor from the user's clothing. Thus, the user can have increased self-confidence and discretion when returning to a public situation.

In still other arrangements, the employed treatment-component may include a powder, a scent, or a deodorizing material, and may include nature extracts or other essences to help improve the user's experience. A suitable deodorizing wipe or other employed treatment-component can, for example include a transition metal salt solutions, such as a solution containing copper chloride, zinc chloride or the like. Deodorizing formulations comprising solutions that contain zinc salts are available from commercial vendors. Other deodorizing wipes may include copper-modified nano-particles in a liquid carrier.

The employed treatment-component may also include a stain remover, stain remover/treatment that is activated in a wash cycle. In a further feature, the cleaning wipe or other employed treatment-component can be configured to deliver a material which can protect the clothing being worn by the user. The wipe can operatively dispense a cleaning agent, a deodorizing agent and/or a protecting agent. The protecting agent can be configured to help prevent the undesired movement of liquids back onto the user's body or through the clothing worn by the user. Conventional protecting agents are well known and available from commercial vendors.

In a particular arrangement, for example, the first treatment-component 56 can be configured to clean bodily waste material from the fabric of a reusable undergarment or outer-garment, and the second treatment-component 58 can be configured to provide a second treatment-type that includes applying a deodorizing material to a person's skin or to an article of clothing. Additionally, a third treatment-component 60 may be configured to provide a third treatment-type that includes applying a powder to a user's skin. Desirably, the powder can include a drying material.

In the various arrangements of the personal care system, each or any of the treatment-components can include a corresponding packet or other operative container which holds the selected treatment-component. For example, the first treatment-component can include a first packet 57 and the second treatment-component can include a second packet 59. In other desired configurations, the third treatment-component can include a third packet 61 and the fourth treatment-component 62 can include a fourth packet 63.

In the various configurations of the invention, the article packet 35 and the component packets (57, 59, 61, 63) can include a pouch, a wrapper, envelope, bag, box, tube, vial, container or the like, as well as combinations thereof. Additionally, each packet can be constructed with any suitable material. For example, the packet material can include a cellulosic paper layer, a polymer film, a nonwoven fabric, a woven fabric or the like, as well as combinations thereof. The packet material can be extensible, substantially non-extensible, stretchable or substantially non-stretchable, as desired. Additionally, one or more of the selected packets may be configured to be flushable. Each packet may also be configured to hold one or more individual components, and may optionally include individual, discrete compartments for separately holding individual components. The individual components may be selected to be the same or different, as desired.

The various wipes employed with the present invention can be provided by any operative wipe component. Such wipes are conventional and well known in the art, and may, for example, comprise one or more layers. The employed layers may include bonded cellulosic fibers, polymer fibers, woven fabrics, nonwoven fabrics, polymer films, foam materials or the like, as well as combinations thereof. Each wipe can be rolled, folded or otherwise reduced in size in any operative manner or configuration when the wipe is assembled into the personal care system. Where a wipe is enclosed in a corresponding packet, for example, the wipe can be folded or otherwise reduced in size when the wipe is incorporated into its packet.

In like fashion, the supplemental absorbent article 34 can be rolled, folded otherwise reduced in size in any operative manner or configuration when the supplemental article is assembled into the personal care system. Where the supplemental absorbent article is enclosed in a corresponding packet, for example, the supplemental absorbent article can be folded otherwise reduced in size when the supplemental article is incorporated into its packet.

Figure 8A:
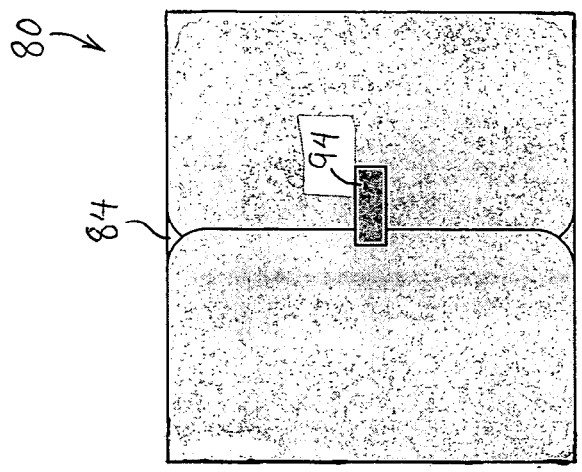
FIG. 8A shows a schematic view of the configuration of the personal care system of FIG. 8 in a completely closed condition.
Figure 8:
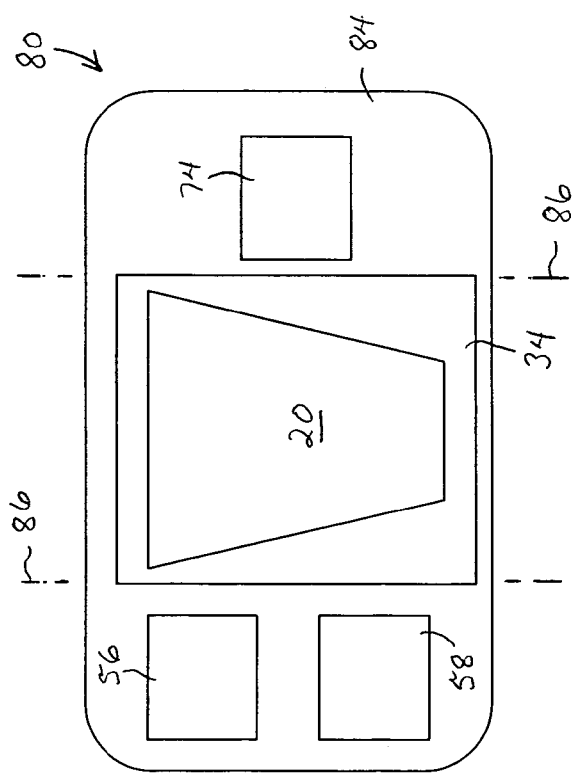
FIG. 8 shows a schematic view of another representative configuration of a personal care system in a fully open condition.

With reference to FIGS. 1, 5 and 8, the kit items can further include a container which has been configured to hold a soiled article of reusable clothing. For example, the assembly mechanism 82 may be configured to provide a bag, pouch, box or other suitable container. Alternatively, a small separately provided disposal bag or other separately provided container 74 may be assembled or otherwise incorporated into the personal care system 80. Optionally, the storage packet (35, 57, 59, 61, 63) employed with one of the other preexisting kit items may be reused to store and contain the soiled reusable garment.

The assembly mechanism 82, which holds the selected kit items together in the desired cooperating, combined unit, can be provided by any suitable mechanism. As representatively shown in FIGS. 1 and 5 through 9A, the assembly mechanism can include a package mechanism, and the package mechanism can be provided by any operative securement or holding system. In desired arrangements, the resulting package can be selectively opened and selectively reclosed, as desired. The package mechanism can, for example, include a packaging wrapper, packet, bag, carton, box, envelope, casing or the like, as well as combinations thereof. The packaging mechanism can include one or more separately provided components and may comprise a composite member. Alternatively, the packaging mechanism may be provided by a packaging component or composite that is integrally formed with a selected portion of a component or member of one or more of the employed kit items. Optionally, the packaging mechanism may include a bond, attachment or other securement between cooperating components of the employed kit items. For example, the packaging mechanism may include a system or arrangement of operative connections between selected packets (35, 57, 59, 61, 63) or other components that are employed in the personal care system 80. The entire package mechanism or portions of the package mechanism may be configured to be flushable.

The resulting package is desirably discreet, with a small size. Additionally, the package can have any desired color, and may be soft, hard, flexible, relatively rigid, resealable, extensible or stretchable. A desired arrangement of the package can include an extensible reclosable package having a neutral color. The package may optionally include sub-packages, include multiple compartments, and may be sealed or scented. The packaging material may also be transparent or translucent, and may be readily flexible and stretchable.

The personal care system 80 can be distinctively sized to provide a small compact package that is easy to transport, use and/or store. The personal care system can have any operative form and shape, and the shape can be regular, irregular, linear or curvilinear, as desired. For example the shape can be oval, egg-shape, rectilinear, triangular, trapezoidal or the like, as well as combinations thereof. In particular aspects, the personal care system, in its assembled and closed condition, can provide a package width 88, a package length 90 and a package thickness 92 (e.g. FIGS. 5B and 5C), all of which are sufficiently small. In particular aspects, the package width 88 can be at least a minimum of about 25 millimeters (mm). The package width can alternatively be at least about 40 mm, and can optionally be at least about 60 mm to provide desired benefits. In other aspects, the package width can be up to a maximum of about 175 mm, or more. The package width can alternatively be up to about 150 mm, and can optionally be up to about 120 mm to provide desired levels of effectiveness. A desired configuration can have a package width of about 90 mm. In further aspects, the package length 90 can be at least a minimum of about 25 mm. The package length can alternatively be at least about 50 mm, and can optionally be at least about 75 mm to provide desired benefits. In other aspects, the package length can be up to a maximum of about 270 mm, or more. The package length can alternatively be up to about 200 mm, and can optionally be up to about 150 mm to provide desired performance. A desired configuration can have a package length of about 100 mm. In still other aspects, the package thickness 92 can be at least a minimum of about 4 mm. The package thickness can alternatively be at least about 10 mm, and can optionally be at least about 15 mm to provide desired benefits. In particular aspects, the package thickness can be up to a maximum of about 51 mm, or more. The package thickness can alternatively be up to about 40, and can optionally be up to about 30 mm to provide desired effectiveness. A desired configuration can have a package thickness of about 25 mm.

The personal care system can also be configured to provide a distinctively low weight. In a particular aspect, the system weight can be at least a minimum of about 2.9 grams (g). The system weight can alternatively be at least about 5 g, and can optionally be at least about 10 g to provide improved [desired] benefits. In other aspects, the system weight can be up to a maximum of about 900 g, or more. The system weight can alternatively be up to about 450 g, and can optionally be up to about 250 g to provide improved [desired levels of] effectiveness. In a particular arrangement, the system weight can be about 13 g.

If the dimensions and weight of the personal care system are outside the desired values, the personal care system can be excessively bulky, heavy or obtrusive. As a result, the packaged system would be cumbersome to transport and store, and would be less able to provide desired levels of discretion.

The disposable panty or other substitute undergarment 20 can be folded into a small shape that approximates the size and shape of the packet that holds the selected, supplemental absorbent article (e.g. a packeted pad or pantiliner). Then, the packets containing the selected treatment-components (e.g. wipes) can be distributed and arranged to form an efficiently small shape that approximates the size and shape of the supplemental absorbent article. The packets containing the treatment components can be bonded or otherwise operatively secured to the packet containing the supplemental absorbent article. The securement may be operatively releasable or may substantially permanent, as desired. In an optional feature, the packets holding the treatment components may have an arrangement that sandwiches the substitute undergarment between two packets. In other features, one or more side regions of the sandwich arrangement can be opened to allow a convenient access to the substitute undergarment. As a result, the configuration of the packet for the supplemental absorbent article, combined with the configuration of the individual packets for each treatment-component (e.g. cleaning wipe), may provide a packaging mechanism that does not require a further, separately provided component or member.

In a particular aspect, the assembly mechanism 82 can be configured to provide an operative package. In another aspect, the package can be configured to provide a desired holding device for storing a soiled reusable garment. The holding device may be integrally formed with the package, or may be a separately provided container 74 (e.g. FIGS. 8–8A). In other aspects, the employed packaging system can also include an operative closure mechanism 94, and may optionally include an odor-control mechanism. The closure mechanism can include any operative fastening mechanism or system. For example, the desired attachments or securements can include interengaging mechanical fasteners, adhesive bonds, cohesive bonds, thermal bonds, ultrasonic bonds, pins, snaps, staples, rivets, stitches, welds, zippers, fastener tapes, fastener tabs, hook-and-loop fasteners or the like, as well as combinations thereof. The odor-control mechanism can, for example, include a deodorant material that is located on or otherwise combined with an interior surface of the package, an odor neutralizing material that is combined with the package material, a separately provided deodorant component, a separately provided odor neutralizing component or the like, as well as combinations thereof.

With reference to FIGS. 1, and 5 through 9A, the personal care system 80 can include an assembly mechanism which allows a selective positioning of the kit items in an open or closed position. The open position can present the kit items for ready use, and the closed position can provide for convenient transport and storage. Additionally, the assembly mechanism can be configured to present the kit items in one or more selected arrays. For example, when the assembly mechanism is in a closed position, the kit items can be present in a first, closed array, and when the assembly mechanism is in an open position, the kit items can be present in a second, open array. As representatively shown, the supplemental absorbent article 34 can be operatively held in a corresponding article packet 35, and the substitute undergarment 20 can be operatively superposed onto the article packet. The substitute undergarment may or may not be enclosed in a corresponding packet or other container, as desired. The first treatment-component 56 can be operatively held in a corresponding first packet 57, and the second treatment-component 58 can be operatively held in its corresponding second packet 59. If employed, the third treatment-component 60 can be operatively held in a corresponding third packet 61, and a fourth treatment-component 62 can be operatively held in a corresponding fourth packet 63.

Each employed component packet can be pivotably connected to a selected perimeter border region of the packet 35 of the supplemental absorbent article 34. For example, each employed component packet (57, 59, 61, 63) can be operatively joined or otherwise operatively connected to a perimeter edge region of the article packet 35 (e.g. FIGS. 5 through 7A). In particular arrangement, each employed component packet (57, 59, 61, 63) can be operatively connected to a corner region of the article packet 35 (e.g. FIGS. 5 through 5B). Each component packet can be selectively moved to its corresponding open or closed position. In the closed position each component packet can be superposed over or onto the article packet 35. Additionally, each component packet can be selectively superposed over or onto the substitute undergarment 20. In the open position, each component packet can be operatively positioned at a location that is relatively outboard of the perimeter border of the article packet 35.

In a particular aspect, the assembly mechanism 82 can include a pivot mechanism that provides the desired pivotable connection which attaches or otherwise assembles the article packet 35 and/or the component packets into the system of the invention. The pivotable connection can be provided by any operative mechanism. For example, the pivotable connection can be provided by a pin-type hinge, a pin-less hinge, a flexure hinge, an embossed hinge region, a folded hinge region or the like, as well as combinations thereof. The pivotable joinder can include a separately provided component, or may be integrally formed from an operative portion of a preexisting component, such as a preexisting portion of the employed package or other assembly mechanism 82, and/or a preexisting portion of one or more of the packets (35, 57, 59, 61, 63).

A further aspect of the personal care system 80 can include an assembly mechanism 82 which is configured to superpose the substitute undergarment over the supplemental absorbent article. Additionally, the assembly mechanism can be configured to superpose the first treatment-component over the supplemental absorbent article, and to superpose the second treatment-component over the supplemental absorbent article.

In another aspect of the personal care system 80, the supplemental absorbent article 34 can include an associated article packet 35, and the first treatment-component 56 can include a corresponding first treatment packet 57. Additionally, the second treatment-component 58 can include a corresponding second treatment packet 59. In further features, the first treatment packet can be pivotably connected to a first region of the article packet, and the second treatment packet can be pivotably connected to a second region of the article packet. For example, the first treatment packet 57 can be pivotably connected to a first side region of the article packet 35, and the second treatment packet 59 can be pivotably connected to a second side region of the article packet (e.g. FIGS. 6–7A).

Still another aspect of the personal care system 80 can include a configuration in which the assembly mechanism 82 further includes a package panel 84, which can include any suitable material. The package panel may be integrally formed with another component of the personal care system, or may be a separately provided member. The package panel may be constructed with one or more layers of suitable materials, and may be a composite material. For example, the package panel can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded-web, a bicomponent spunbond fabric or the like as well as combinations thereof. For example, the package panel can include a woven fabric, a nonwoven fabric, a polymeric film, or the like, as well as combinations thereof. Other examples of suitable materials for constructing the package panel can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. The package panel can be configured to be liquid-permeable or operatively liquid-impermeable, as desired.

Figure 9A:
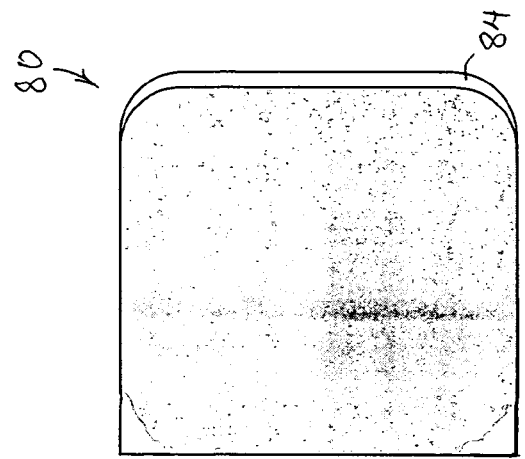
FIG. 9A shows a schematic view of the configuration of the personal care system of FIG. 9 in a completely closed condition.
Figure 9:
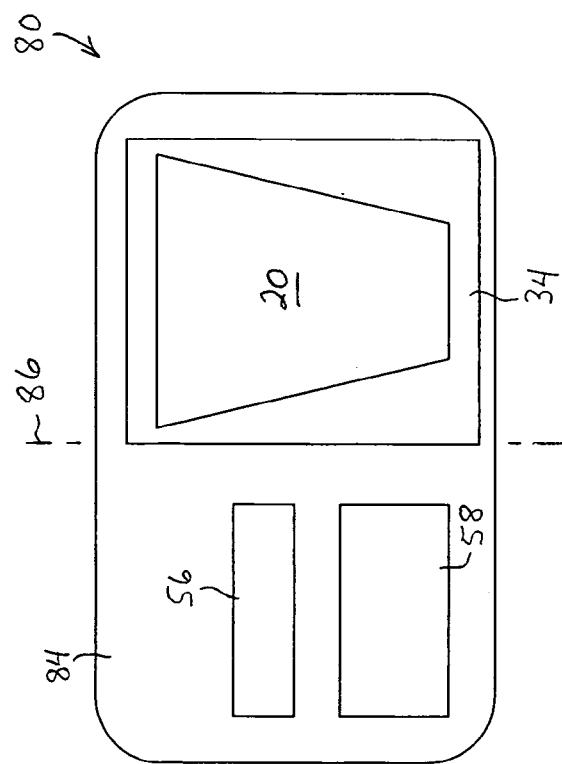
FIG. 9 shows a schematic view of another representative configuration of a personal care system in a fully open condition.

In a desired aspect, the package panel 84 can operatively enclose the substitute undergarment 20 and the first and second treatment-components into the desired assembly with the supplemental absorbent article 34. With reference to FIGS. 8–9A, the package panel 86 can be configured to pivotably connect to the article packet 35, and to hold the first and second treatment components over the article packet when the package panel is moved to an appointed, closed position. The package panel can, for example, include one folding line (e.g. FIGS. 9–9A), or a plurality of folding lines (e.g. FIGS. 8–8A). Additionally, a selected closure mechanism 94 can be employed and operatively configured to hold the personal care system in the desired closed position. In a further feature, the package panel 84 may be sized and configured such that the supplemental absorbent article can be superposed on at least a portion of the package panel 86. Accordingly, the closure mechanism can hold the personal care system in closed arrangement that resembles a small, closed wallet.

In the construction of the various components, such as the substitute undergarment 20, supplemental absorbent article 34 and/or assembly mechanism 82 (e.g. package), the components may be assembled and held together with any operative securement mechanism or system. For example, the desired attachments or securements can include adhesive bonds, cohesive bonds, thermal bonds, ultrasonic bonds, pins, bonding tapes snaps, staples, rivets, stitches, welds, zippers, or the like, as well as combinations thereof.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A personal care system, comprising a plurality of kit items; and an assembly mechanism which holds the kit items together in a cooperating combination; wherein the kit items include a substitute undergarment;

a supplemental absorbent article configured for cooperative use when located in the crotch region of the substitute undergarment, the supplemental absorbent article including a backsheet, and a liquid-permeable topsheet which is operatively connected in a facing relation with the backsheet;

a first treatment-component configured to provide a first treatment-type;

at least a second treatment-component configured to provide a second treatment-type that differs from the first treatment-type;

and wherein the supplemental absorbent article includes an article packet;

the first treatment-component includes a first treatment packet;

the second treatment-component includes a second treatment packet the first treatment packet is pivotably connected to a first region of the article packet;

the second treatment packet is pivotably connected to a second region of the article packet.

2. A personal care system as recited in claim 1, wherein the first treatment-component is configured to clean bodily waste material from a fabric.

3. A personal care system as recited in claim 1, wherein the first treatment-component is configured to clean bodily waste material from a reusable, outer-garment.

4. A personal care system as recited in claim 1, wherein the first treatment-component is a dry-component configured to provide a first treatment-type that cleans bodily waste material from a reusable, outer-garment.

5. A personal care system as recited in claim 1, wherein the first treatment-component is a wet-component configured to provide a first treatment-type that cleans bodily waste material from a reusable, outer-garment.

6. A personal care system as recited in claim 1, wherein the first treatment-component includes a packet which holds the first treatment-component.

7. A personal care system as recited in claim 1, wherein the second treatment-component includes a packet which holds the second treatment-component.

8. A personal care system as recited in claim 1, wherein the second treatment-component is configured to provide a second treatment-type that includes applying a deodorizing material to en article of clothing.

9. A personal care system as recited in claim 1, wherein the kit items further include a container for holding a soiled article of reusable clothing.

10. A personal care system as recited in claim 1, wherein the supplemental absorbent article includes a packet which holds the supplemental absorbent article.

11. A personal care system as recited in claim 1, wherein the kit items further include a third treatment-component configured to provide a third treatment-type that differs from said first and second treatment-types.

12. A personal care system as recited in claim 11, wherein the kit items further include a fourth treatment-component configured to provide a fourth treatment-type that differs from said first, second and third treatment-types.

13. A personal care system as recited in claim 1, wherein the kit items further include a third treatment-component configured to provide a third treatment-type that includes applying a powder material to a user's skin.

14. A personal care system as recited in claim 1, wherein the assembly mechanism is configured to
superpose the substitute undergarment over the supplemental absorbent article;
superpose the first treatment-component over the supplemental absorbent article; and
superpose the second treatment-component over the supplemental absorbent article.

15. A personal care system as recited in claim 14, wherein the assembly mechanism further includes a package panel which operatively encloses the substitute undergarment and the first and second treatment-components into an assembly with the supplemental absorbent article.

16. A personal care system, comprising a plurality of kit items; and an assembly mechanism which holds the kit items together in a cooperating combination; wherein the kit items include
a substitute undergarment;
a supplemental absorbent article configured for cooperative use when located in the crotch region of the substitute undergarment, the supplemental absorbent article including an absorbent body and a topsheet which is operatively connected with the absorbent body;
a first wipe configured to provide a first treatment-type to a fabric; and
at least a second wipe configured to provide a second treatment-type to the fabric, the second treatment-type differing from the first treatment-type;
and wherein
the supplemental absorbent article includes an packet;
the first wipe includes a first treatment packet;
the second wipe includes a second treatment packet;
the first treatment packet is pivotably connected to a first region of the article packet;
the second treatment packet is pivotably connected to a second region of the article packet.

17. A personal care system as recited 16, further comprising a third wipe configured to provide a third treatment-type which differs from the first and second treatment-type.

18. A personal care system as recited in claim 16, further comprising
a third wipe configured to provide a third treatment-type, which differs from the first and second treatment-type; and
a fourth wipe configured to provide a fourth treatment-type, which differs from the first, second and third treatment-types.

19. A personal care system as recited in claim 16, further comprising
a third wipe configured to provide a third treatment-type to a wearer of the substitute undergarment;
a fourth wipe configured to a fourth treatment-type to the wearer of the substitute undergarment;
wherein
the third treatment-type differs from the first and treatment-type; and the fourth treatment-type differs from the first, second and third treatment-types.

* * * * *